(12) United States Patent
Castro

(10) Patent No.: US 12,127,768 B2
(45) Date of Patent: Oct. 29, 2024

(54) SURGICAL FASTENER

(71) Applicant: Blue Sky Technologies, LLC, Louisville, KY (US)

(72) Inventor: Frank Castro, Louisville, KY (US)

(73) Assignee: BLUE SKY TECHNOLOGIES, LLC

( * ) Notice: Subject to any disclaimer, the term of this patent is extended or adjusted under 35 U.S.C. 154(b) by 443 days.

(21) Appl. No.: 17/770,671

(22) PCT Filed: Oct. 24, 2020

(86) PCT No.: PCT/US2020/057235
§ 371 (c)(1),
(2) Date: Apr. 21, 2022

(87) PCT Pub. No.: WO2021/162758
PCT Pub. Date: Aug. 19, 2021

(65) Prior Publication Data
US 2022/0361924 A1   Nov. 17, 2022

Related U.S. Application Data

(60) Provisional application No. 62/975,248, filed on Feb. 12, 2020.

(51) Int. Cl.
*A61B 17/86*  (2006.01)
*A61B 17/16*  (2006.01)
*A61B 17/70*  (2006.01)
*A61B 17/84*  (2006.01)

(52) U.S. Cl.
CPC .......... *A61B 17/7055* (2013.01); *A61B 17/16* (2013.01); *A61B 17/1617* (2013.01); *A61B 17/7032* (2013.01); *A61B 17/7035* (2013.01); *A61B 17/84* (2013.01); *A61B 17/844* (2013.01); *A61B 17/8605* (2013.01); *A61B 17/8625* (2013.01); *A61B 17/8635* (2013.01); *A61B 2017/8655* (2013.01)

(58) Field of Classification Search
CPC ............ A61B 17/7055; A61B 17/8625; A61B 17/8635; A61B 17/8095; A61B 17/846; A61B 17/686; A61B 2017/0647
See application file for complete search history.

(56) References Cited

U.S. PATENT DOCUMENTS

| | | | |
|---|---|---|---|
| 3,887,186 A | 6/1975 | Matlock | |
| 6,770,096 B2 | 8/2004 | Bolger et al. | |
| 6,855,168 B2 | 2/2005 | Crozet | |
| 8,100,972 B1 | 1/2012 | Bruffey et al. | |
| 8,328,870 B2 | 12/2012 | Patel et al. | |
| 8,545,562 B1 | 10/2013 | Materna et al. | |
| 9,421,112 B2 | 8/2016 | Bal et al. | |
| 10,159,516 B2 | 12/2018 | Tan | |
| 10,405,872 B2 | 9/2019 | Victor et al. | |
| 10,772,738 B2 | 9/2020 | Castro | |
| 2009/0265006 A1* | 10/2009 | Seifert | A61B 17/025 623/17.11 |
| 2020/0305896 A1* | 10/2020 | Castro | A61B 17/84 |

* cited by examiner

*Primary Examiner* — Olivia C Chang
(74) *Attorney, Agent, or Firm* — BUSINESS PATENT LAW, PLLC

(57) ABSTRACT

A surgical fastener provided with a curved cutter, an anterior wedge-like tip and a surgeon facing end. Among other things, the surgical fastener's cutter can cut bone or other tissue.

20 Claims, 4 Drawing Sheets

SURGICAL FASTENER

BACKGROUND OF THE INVENTION

A. Field of the Invention

The present invention is surgical fastener provided with a curved cutter, an anterior wedge-like tip, a front end and a surgeon facing end. In select preferred embodiments, a head extends from the surgeon facing end. The head can be fixed or polyaxial. Except for the head, the surgical fastener is threadless.

B. Description of the Previous Art

Any discussion of references cited in this Description of the Previous Art merely summarizes the disclosures of the cited references and Applicant makes no admission that any cited reference or portion thereof is relevant prior art. Applicant reserves the right to challenge the accuracy, relevancy and veracity of the cited references.

References that may indicate a state-of-the-art include: 1) U.S. Pat. No. 3,887,186—Matlock Jr. discloses a broadhead; 2) U.S. Pat. No. 8,100,972—Bruffey, et al. discloses a spinal cage having deployable member; 3) U.S. Pat. No. 8,545, 562—Materna et al.; 4) U.S. Pat. No. 9,421,112—Bal, et al. discloses a fixation system for spinal cages; 5) U.S. Pat. No. 10,159,516—Tan discloses an interchangeable orthopedic blade; 6) U.S. Pat. No. 10,405,872—Victor, et al. and 7) US Published Patent Application 20090265006—Seifert, et al. discloses a lateral spinous process spacer.

Among other things, none of the above listed references, alone or in combination, disclose a surgical fastener comprising: a) a wedge-like tip comprising a frontal edge; the wedge-like tip positioned at a first end of a cutter and adapted to engage a joint space or a portion of a surgically created cavity or the joint space; b) a longitudinal axis (X-X) extending from the wedge-like tip through the first end and a surgeon facing end of the cutter; c) the cutter comprising: i) a first section distinct from the wedge-like tip and a second section distinct from the wedge-like tip; the first and second sections extending outward in lateral planes from the longitudinal axis (X-X); ii) a first curvature of the first section extending the length of the cutter from a first lengthwise end proximate the first end to a second lengthwise end proximate the surgeon facing end; the first curvature including a first outermost point distal from the longitudinal axis (X-X); and iii) a second curvature of the second section extending the length of the cutter from a first lengthwise end proximate the first end to a second lengthwise end proximate the surgeon facing end; the second curvature including a second outermost point distal from the longitudinal axis (X-X); d) the first section further comprising a first cutting edge to cut a biological structure and a first noncutting edge opposed from the first cutting edge, wherein the first cutting edge comprises a concave bend relative to the opposed first noncutting edge; e) the second section further comprising a second cutting edge to cut the biological structure and a second noncutting edge opposed from the second cutting edge, wherein the second cutting edge comprises a concave bend relative to the opposed second noncutting edge; and f) the surgeon facing end further comprising: i) an intermediate segment with the longitudinal axis extending therethrough; ii) a first segment connected with the intermediate segment and the second lengthwise end of the first curvature; and iii) a second segment connected with the intermediate segment and the second lengthwise end of second curvature, wherein the intermediate segment, the first segment and the second segment create the surgeon facing end consisting of the intermediate, first and second segments.

SUMMARY OF THE INVENTION

Successful fusion of a joint or broken bone is directly correlated to the construct rigidity surrounding the area of interest. Current spinal instrumentation relies on screws being anchored into bone and rods connecting to these anchors. Loosening of current constructs occurs primarily at the bone-anchor interface. Toggling of the screws can allow for enlargement of the insertion pathway. As the diameter of the insertion pathway increases, there is greater risk of the screw backing out and construct failure. The current invention can be utilized for arthrodesis procedures of the cervical, thoracic and lumbar spine, as well as the sacroiliac joint or other similar joints.

The biomechanical strength of traditional threaded fixation screws is dependent upon several design characteristics. Larger diameter screws are stronger and more difficult to extract due to increased surface area (friction). The thread pitch, or difference between the inner diameter and the outer diameter, also influences resistance to pull out or back out. The larger the pitch, the greater the resistance to pull out. Biomechanical studies have demonstrated that the volume of bone between screw threads can influence the screw's resistance to pull out. Those skilled in the art recognize that the type and quality of bone are important variables influencing resistance to pull out. Patients with osteoporotic bone have significantly less dense bone than patients with normal bone densities. The contribution of the cancellous bone between the screw threads in patients with osteoporosis is less than patients of normal bone density. In some osteoporotic patients, the screw's fixation strength and resistance to pull out can be determined by the volume of cortical bone in one or two threads of a traditional fixation screw.

Long surgical constructs, such as those used for scoliosis or deformity correction surgery, are often anchored into the sacrum or ilium. These constructs are usually anchored with a large diameter threaded screw. The biophysical forces transmitted to these implanted screws can lead to loosening, construct failure, pain and additional revision surgery.

Many of traditional surgical screws include thread lengths of one to two millimeters that determine the screw's fixation strength. The current surgical fastener provides a potential fixation surface area of from about three to about ten times more than traditional fixation screws. In use, the potential surface area of the surgical fastener is generally juxtaposed the cortical bone—the patient's strongest bone. The current invention can be provided with surface treatments and apertures that can encourage bone ingrowth, long-term construct stability and arthrodesis.

Unlike other joint implants, among other things, the present surgical fastener can include a curvilinear cutter. Such structures can cut bone and other tissues. Depending on surgical requirements, the surgical fastener can be anchored into the cervical spine, sacrum, the ilium or the sacroiliac joint.

Preferred embodiments of the surgical fastener, among other things, can include an anterior edge wedge-like tip, cutter and head.

The anterior wedge-like tip can separate surfaces or a joint, such as the sacroiliac joint or posterior cervical joint or the frontal edge can cut cortical bone. When rotated, the surgical fastener can be adapted to cut cartilage, cortical bone or other tissues that can provide exposure of bone to another bony surface. Exposing two bony surfaces can increase the probability the bony surfaces of the surfaces uniting into a solid fusion. The cutter may facilitate reapproximation of two joint surfaces that have experienced a distractive deformity from trauma or tumor. Prior to cutting through the first articular surface, the cutter can guide the bone back towards its anatomic position. Once the cutter crosses both articular surfaces, forward pressure on the cutter compresses the two surfaces and the curved cutter can prevent retropulsion. When the cutter is placed across a joint, it may also facilitate fusion by exposing a conduit for bone to form across the joint. When the cutter is positioned completely across a joint, it may compress the articular or bony surfaces. Such imposed motion limitation may result in joint ankylosis.

Among other things, the surgical fastener's head can: limit the depth the fastener can be inserted through the incision into the surgically created cavity or joint space; be connected with other surgical apparatus, such as, rods, plates or other fixation devices; and relative to a headless screw, apply increased torque to the cutter.

Intentional or unintentional rotation of threaded devices can lead to displacement of the device into or towards an undesirable location resulting in damage or dysfunction to either a nerve or blood vessel. Those skilled in the art recognize that expulsion of a surgical screw results in an unstable screw that can increase the risk of non-fusion or spinal deformity. Among other things, the surgical fastener can be provided with a head of sufficient area to prevent over-insertion into the surgically created cavity or joint space. Depending on medical and/or surgical parameters, the current invention can be adapted to either compress or distract a joint. By way of illustration, when distraction of the posterior cervical facet joint occurs, the adjacent neuroforamin is enlarged and indirect decompression of the exiting nerve root can occur.

Subsequent to insertion into a surgically created cavity or joint space with adequate outward tissue remaining proximate the insertion point, rotating the surgical fastener from about 30 degrees to about 150 degrees can improve the surgical fastener's resistance to pull out forces.

An aspect of the present invention is to provide a surgical fastener.

Still another aspect of the present invention is to provide a surgical fastener with a wedge-like tip and a head opposite the wedge-like tip.

It is yet another aspect of the present invention to provide a surgical fastener with either a fixed head or a polyaxial head.

Still another aspect of the present invention is to provide a surgical fastener with a receiver adapted to receive an apparatus distinct from the surgical fastener.

It is still another aspect of the present invention to provide a surgical fastener with a cutter including first and second sections with cutting edges to cut the biological structure or tissue and an opposed noncutting edges.

Yet still another aspect of the present invention is to provide a surgical fastener with a cutter including first and second sections where each section includes a cutting edge with a concave bend relative to the noncutting edge.

Still another aspect of the present invention is to provide a surgical fastener with a cutter including first and second sections, where relative to the longitudinal axis, each section includes a first curvature that curves from a first point more proximate the longitudinal axis toward a second point more distance from the longitudinal axis.

It is still another aspect of the present invention to provide a surgical fastener where only the head is provided with threads.

A preferred embodiment of the current invention can be described as a surgical fastener comprising: a) a wedge-like tip positioned at a first end of a cutter; the wedge-like tip adapted to engage a joint space or a portion of a surgically created cavity or the joint space; b) a longitudinal axis (X-X) extending from the wedge-like tip through the cutter and a receiver positioned in a surgeon facing end of the cutter; the receiver adapted to receive an apparatus distinct from the surgical fastener; c) the cutter comprising a first section and a second section positioned on opposed sides of the longitudinal axis (X-X), wherein each section is distinct from the wedge-like tip and extends the length of the cutter from the first end to the surgeon facing end opposed from the first end such that the first and second sections are adapted to cut radially relative to the longitudinal axis (X-X); d) the first section further comprising a first cutting edge to cut a biological structure and a first noncutting edge opposed from the first cutting edge, wherein the first cutting edge comprises a concave bend relative to the opposed first noncutting edge and a first curvature extending between the first end and the surgeon facing end of the cutter, wherein, relative to the longitudinal axis (X-X), the first curvature curves from a first point more proximate to the longitudinal axis (X-X) to a second point, proximate the surgeon facing end, more distant from the longitudinal axis (X-X) than the first point and the concave bend runs from the first end proximate the wedge-like tip to the surgeon facing end; and e) the second section further comprising a second cutting edge to cut the biological structure and a second noncutting edge opposed from the second cutting edge, wherein the second cutting edge comprises a concave bend relative to the opposed second noncutting edge and a second curvature extending between the first end and the surgeon facing end of the cutter, wherein, relative to the longitudinal axis (X), the second curvature curves from a first point more proximate to the longitudinal axis (X) to a second point, proximate the surgeon facing end, more distant from the longitudinal axis (X-X) than the first point and the concave bend runs from the first end proximate the wedge-like tip to the surgeon facing end, wherein rotation of the surgical implant connects the surgical implant to the joint space or a portion of the surgically created cavity or the joint space.

Another preferred embodiment of the current invention can be described as a surgical fastener comprising: a) a wedge-like tip positioned at a first end of a cutter; the wedge-like tip adapted to engage a joint space or a portion of a surgically created cavity or the joint space; b) a longitudinal axis (X-X) extending from the wedge-like tip through the cutter and a head connected with a surgeon facing end of the cutter; the head adapted to receive an apparatus distinct from the surgical fastener; c) the cutter comprising a first section and a second section positioned on opposed sides of the longitudinal axis (X-X), wherein each section is distinct from the wedge-like tip and extends the length of the cutter from the first end to the surgeon facing end opposed from the first end such that the first and second sections are adapted to cut radially relative to the longitudinal axis (X-X); d) the first section further comprising a first cutting edge to cut a biological structure and a first noncutting edge opposed from the first cutting edge, wherein the first cutting edge comprises a concave bend relative to the opposed first noncutting edge and a first curvature extending between the first end and the surgeon facing end of the cutter, wherein, relative to the longitudinal axis (X-X), the first curvature curves from a first point more proximate to the longitudinal axis (X-X) to a second point, proximate the surgeon facing end, more distant from the longitudinal axis (X-X) than the first point and the concave bend runs from the first end proximate the wedge-like tip to the surgeon facing end; and e) the second section further comprising a second cutting edge to cut the biological structure and a second noncutting edge opposed from the second cutting edge, wherein the second cutting edge comprises a concave bend relative to the opposed second noncutting edge and a second curvature extending between the first end and the surgeon facing end of the cutter, wherein, relative to the longitudinal axis (X-X), the second curvature curves from a first point more proximate to the longitudinal axis (X-X) to a second point, proximate the surgeon facing end, more distant from the longitudinal axis (X-X) than the first point and the concave bend runs from the first end proximate the wedge-like tip to the surgeon facing end (154), wherein rotation of the surgical implant connects the surgical implant to the joint space or a portion of the surgically created cavity or the joint space.

Still another preferred embodiment of the current invention can be described as a surgical fastener comprising: a) a wedge-like tip comprising a frontal edge; the wedge-like tip positioned at a first end of a cutter and adapted to engage a joint space or a portion of a surgically created cavity or the joint space; b) a longitudinal axis (X-X) extending from the wedge-like tip through the first end and a surgeon facing end of the cutter; c) the cutter comprising: i) a first section distinct from the wedge-like tip and a second section distinct from the wedge-like tip; the first and second sections extending outward in lateral planes from the longitudinal axis (X-X); ii) a first curvature of the first section extending the length of the cutter from a first lengthwise end proximate the first end to a second lengthwise end proximate the surgeon facing end; the first curvature including a first outermost point distal from the longitudinal axis (X-X); and iii) a second curvature of the second section extending the length of the cutter from a first lengthwise end proximate the first end to a second lengthwise end proximate the surgeon facing end; the second curvature including a second outermost point distal from the longitudinal axis (X-X); d) the first section further comprising a first cutting edge to cut a biological structure and a first noncutting edge opposed from the first cutting edge, wherein the first cutting edge comprises a concave bend relative to the opposed first noncutting edge; e) the second section further comprising a second cutting edge to cut the biological structure and a second noncutting edge opposed from the second cutting edge, wherein the second cutting edge comprises a concave bend relative to the opposed second noncutting edge; and f) the surgeon facing end further comprising: i) an intermediate segment with the longitudinal axis extending therethrough; ii) a first segment connected with the intermediate segment and the second lengthwise end of the first curvature; and iii) a second segment connected with the intermediate segment and the second lengthwise end of second curvature, wherein the intermediate segment, the first segment and the second segment create the surgeon facing end consisting of the intermediate, first and second segments.

It is the novel and unique interaction of these simple elements which creates the surgical fastener within the ambit of the present invention. Pursuant to the Articles of the Patent Cooperation Treaty and/or Title 35 of the United States Code, select preferred embodiments of the current invention follow. However, it is to be understood that the descriptions of the preferred embodiments do not limit the scope of the present invention.

DESCRIPTION OF THE PREFERRED EMBODIMENTS

Figure 1:
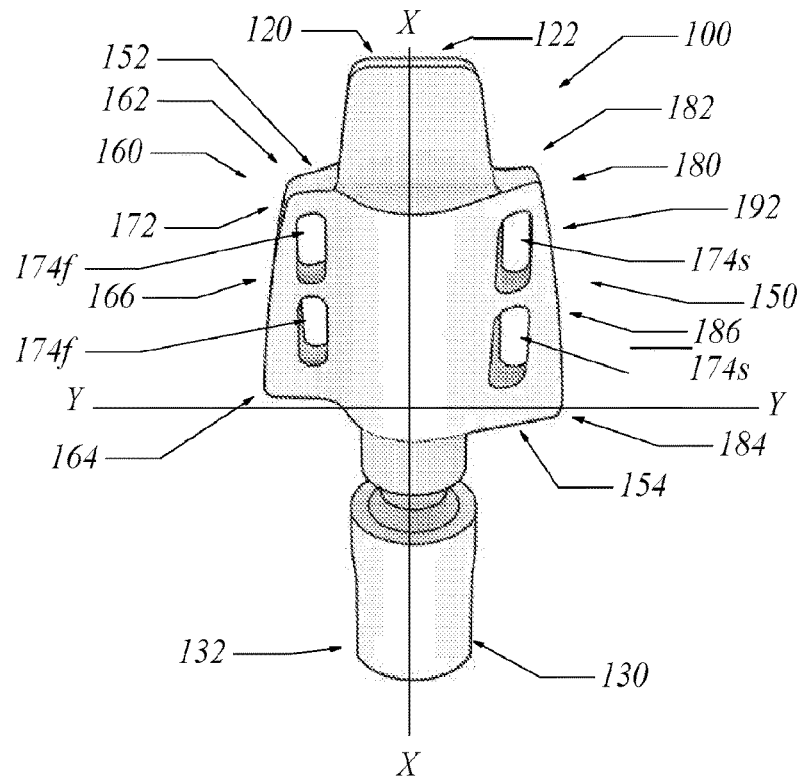
FIG. 1 is a perspective of a preferred embodiment of surgical fastener (100).

Although the disclosure hereof is detailed to enable those skilled in the art to practice the invention, the embodiments published herein merely exemplify the present invention.

As used herein, with respect to the surgical fastener (100): 1) "anterior" of the surgical fastener (100) means the end of the surgical fastener most distant from the surgeon and 2) "posterior or surgeon-facing end" of the surgical fastener (100) means the end of the surgical fastener nearest the surgeon.

In the most general sense, the present invention can result in joint arthrodesis where the surgical fastener is surgically inserted into or across a joint space. Depending on surgical parameters one or more surgical fasteners can be associated with the same surgically created cavity or joint space. The current surgical fastener can be useful for surgeries that can assist in stabilizing injured, deformed and or degenerative joints. Preferred embodiments of the current invention can be employed with ankle, cervical, hand, skull, sacroiliac or other orthopaedic procedures. It appears that the present system is particularly useful for posterior fusions from the occipital region to the pelvis, including the sacroiliac joints. However, the current invention can also be used to fuse the tibia to the talus, the talus to the calcaneus, and metacarpals to the phalanges.

Preferred embodiments of the current surgical fasteners can be manufactured of titanium alloys, stainless steel, non-resorbable polymers or any other composition acceptable in the art. Meeting a long felt but unfilled need in the orthopaedic surgical arts, the novel and unique structures of the present surgical fastener allow the surgical team to, among other things, simplify previous procedures.

The present invention has an anterior end with an anterior wedge-like tip, a cutter and a head, all of which coincide with the longitudinal axis of the surgical fastener. The anterior edge of the surgical fastener is capable of dissecting through adipose, muscle, bone, and/or joint capsule tissues.

The rotatable cutter of the surgical fastener is capable of cutting cartilage and bone and can be associated with the creation of the surgical cavity. Further, the rotatable cutter can morselize bone in preparation for fusion. The combination of the wedge-like tip, rotatable cutter and head of the surgical fastener meet long felt but unfilled needs in the orthopedic surgical arts of, among other things, allowing the surgeon to simplify the previous operating procedures utilized for posterior cervical, sacroiliac, and other joint fusions.

The cutting edges of the surgical fastener are capable of cutting cartilage and bone and can be associated with the creation of the surgical cavity. In select preferred embodiments, cutting edges are distal from the longitudinal axis. Further, the rotatable cutting edges can morselize bone in preparation for fusion. The cutter of the current surgical fastener can be supplied with one or more apertures.

A head can be connected to the surgeon facing end of the cutter. The head can be provided with a receptacle and slots adapted to receive an apparatus distinct from the surgical fastener. Some preferred embodiments include an extender connecting the head to the shaft. Depending on surgical requirements, the head can be either a fixed or polyaxial. And still other embodiments of the cutter can be provided with a receiver adapted to receive an apparatus distinct from the surgical fastener.

Figure 2:
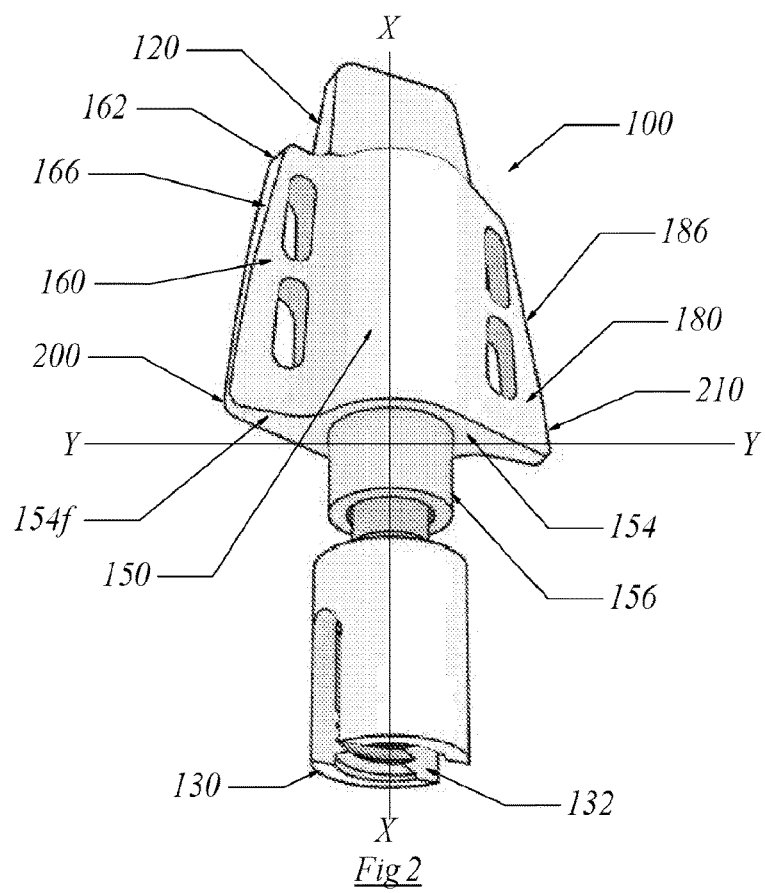
FIG. 2 is a second perspective of the FIG. 1 preferred embodiment of surgical fastener (100) where surgical fastener (100) was rotated approximately 45 degrees.
Figure 3:
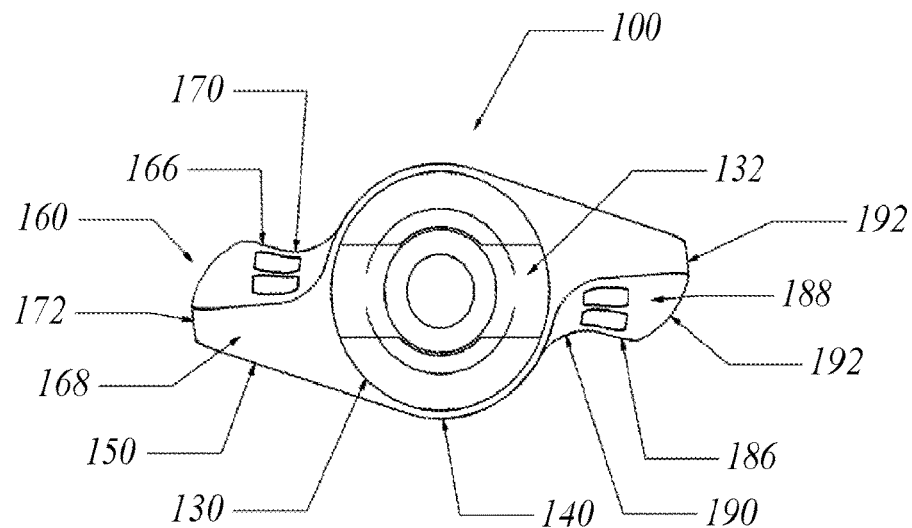
FIG. 3 is a cross-section of FIG. 1 along axis Y-Y that shows concave bend (170) and first curvature (172) of first section (160) and concave bend (190) and second curvature (192) of second section (180) where head (130) is removed from surgical fastener (100).

FIGS. 1 and 2 are perspectives of surgical fastener (100). FIG. 3 is a cross-section of FIG. 1 along axis Y-Y that shows concave bend (170) and first curvature (172) of first section (160) and with head (130) removed from surgical fastener (100). Surgical fastener (100) includes wedge-like tip (120), head (130) and cutter (150).

Wedge-like tip (120) is positioned at first end (152) of cutter (150). The wedge-like tip (120) is adapted to engage the space between a joint or a portion of a surgically created cavity or a joint space (not shown). Depending on surgical parameters, frontal edge (122) can be either dull, sharp or a combination thereof.

With a view toward FIGS. 1, 2 and 5-8, in select preferred embodiments, head (130) is connected to surgeon facing end (154), opposed from first end (152) of cutter (150). Head (130) is provided with receptacle (132) adapted to receive an apparatus (not shown) distinct from the surgical fastener (100). Examples of apparatus received by receptacle (132) include insertion drivers that can advance the surgical fastener into or across a joint space, rods used to connect fasteners positioned at other spinal levels, and removal tools if surgical revision is required. Preferred embodiments of the current surgical fastener (100) can include fixed or polyaxial heads. When a polyaxial head (130) is utilized, an extender (156) extending from surgeon facing end (154) of cutter (150) can expand the multiplanar range motion of polyaxial head (130).

Figure 4:
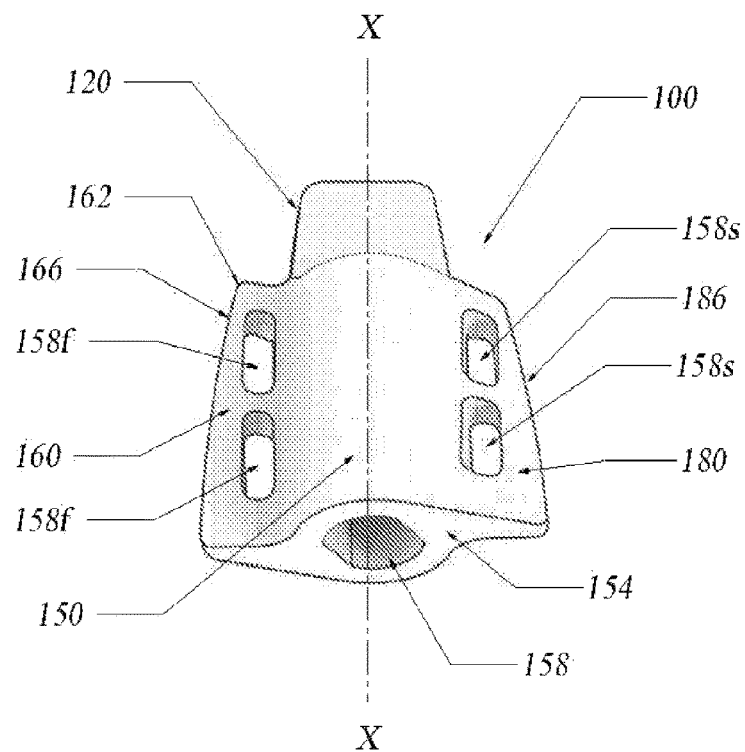
FIG. 4 is a perspective of surgeon facing end (154) of cutter (150) including a receiver (158).

As shown in FIG. 4, in select preferred embodiments, surgeon facing end (154) of cutter (150) can be provided with receiver (158) to receive an apparatus distinct from the surgical fastener (100). Use of receiver (158) can eliminate the use of head (130) in operation of the surgical fastener (100).

With reference to FIGS. 1-8, cutter (150) can be divided into opposed sections (160, 180). Opposed sections (160, 180) are disposed longitudinally along axis X-X and between wedge-like tip (120) and head (130). First section (160) and second section (180) are adapted to cut radially relative to longitudinal axis X-X. For select preferred embodiments, wedge-like tip (120), head (130) and cutter (150) are an integrally formed surgical fastener (100). In other select preferred embodiments, wedge-like tip (120) and cutter (150) create an integral surgical fastener (100).

First section (160) includes a first lengthwise end (162) and an opposed second lengthwise end (164). First section (160) is also provided with a first cutting edge (166) to cut a biological structure or tissue and a first noncutting edge (168) opposed to first cutting edge (166). As best shown in FIG. 3, first cutting edge (166) can be provided with a concave bend (170) relative to first noncutting edge (168). In a first plane distinct from concave bend (170), first section (160) can include a first curvature (172) extending between the first lengthwise end (162) and the second lengthwise end (164). In select preferred embodiments of surgical fastener (100), relative to longitudinal axis X-X, the first curvature (172) curves from a first point more proximate the longitudinal axis X-X toward a second point more distance from the longitudinal axis X-X. Among other things, it is believed that combination of concave bend (170) and first curvature (172) allows for graduated cutting of biological structures.

Second section (180) includes a first lengthwise end (182) and an opposed second lengthwise end (184). Second section (180) is also provided with a second cutting edge (186) to cut a biological structure or tissue and a second noncutting edge (188) opposed to first cutting edge (186). As best shown in FIG. 3, second cutting edge (186) can be provided with a concave bend (190) relative to second noncutting edge (188). In a first plane distinct from concave bend (190), second section (180) can include a second curvature (192) extending between the first lengthwise end (182) and the second lengthwise end (184). In select preferred embodiments of surgical fastener (100), relative to longitudinal axis X-X, the second curvature (192) curves from a first point more proximate the longitudinal axis X-X toward a second point more distance from the longitudinal axis X-X. Among other things, it is believed that combination of concave bend (190) and first curvature (192) allows for graduated cutting of biological structures.

Figure 5:
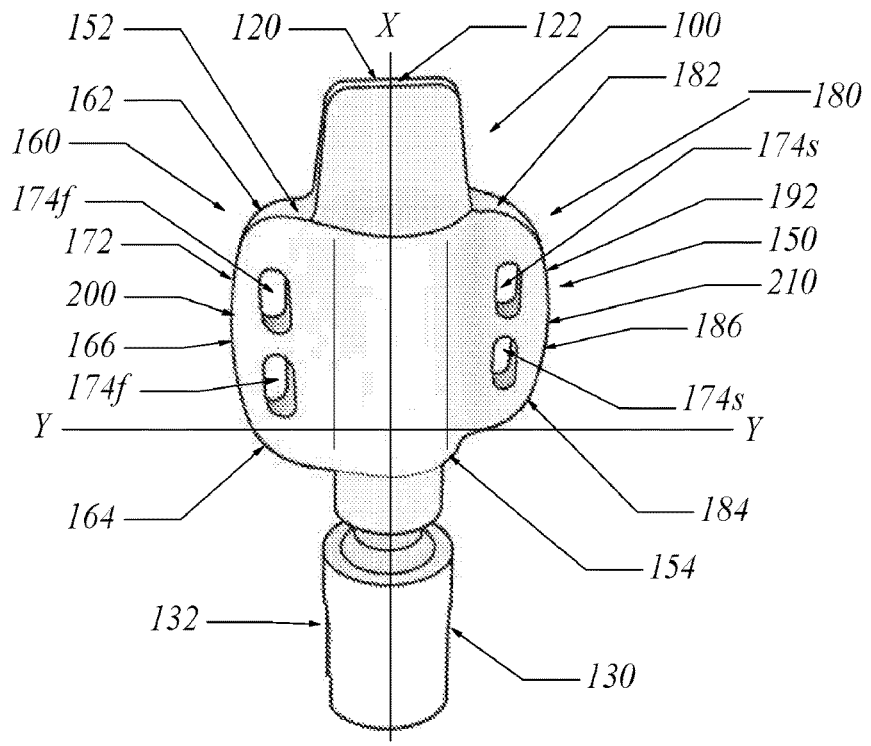
FIG. 5 is a perspective of another preferred embodiment of surgical fastener (100).
Figure 6:
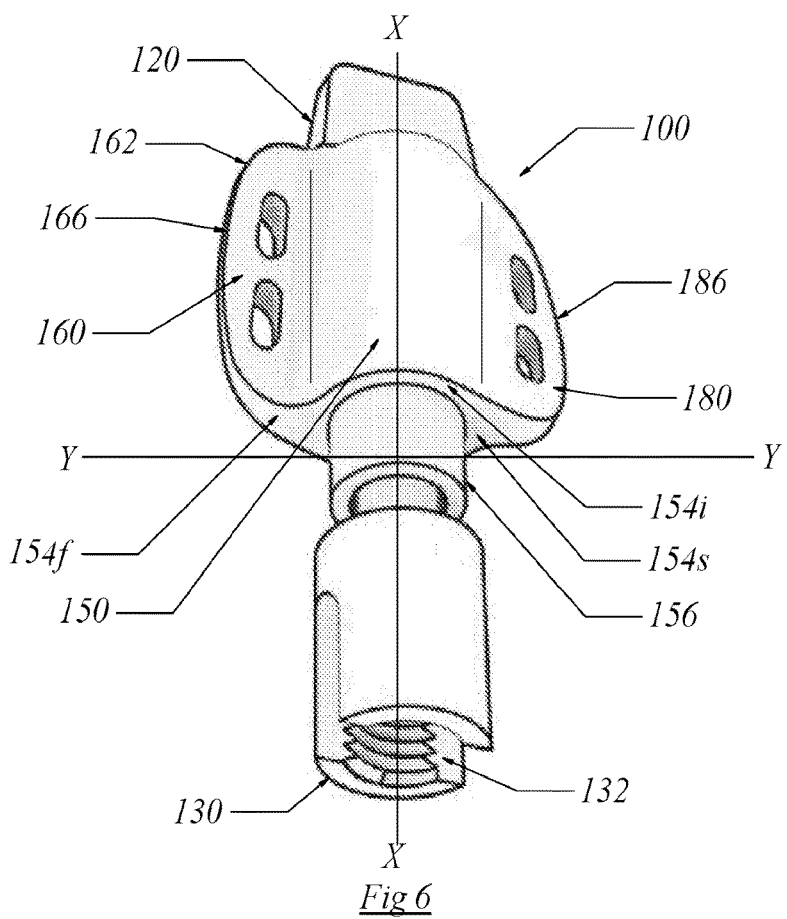
FIG. 6 is a second perspective of the FIG. 5 preferred embodiment of surgical fastener (100) where surgical fastener (100) was rotated approximately 45 degrees.
Figure 7:
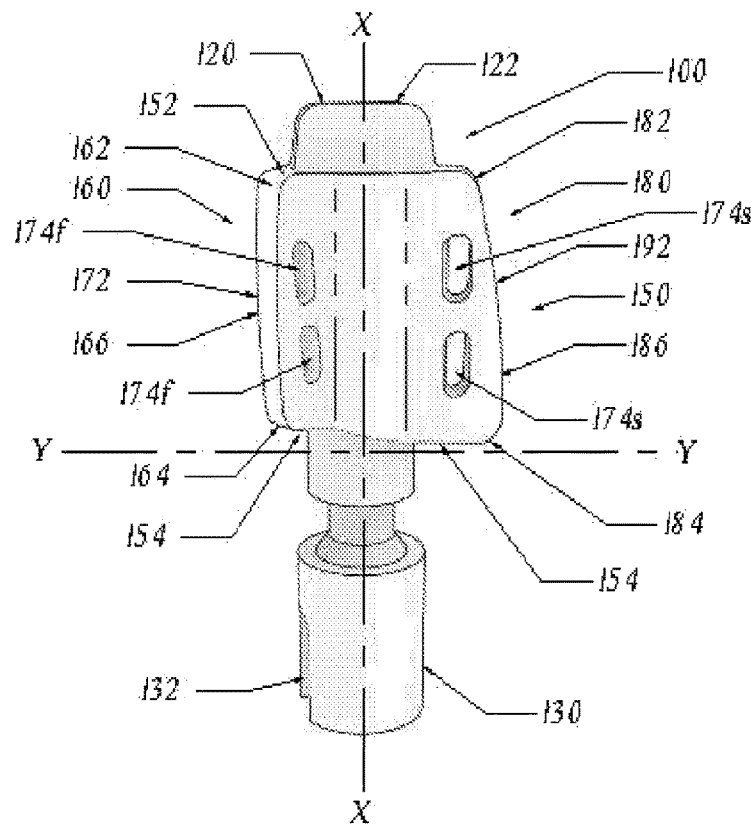
FIG. 7 is a perspective of another preferred embodiment of surgical fastener (100).
Figure 8:
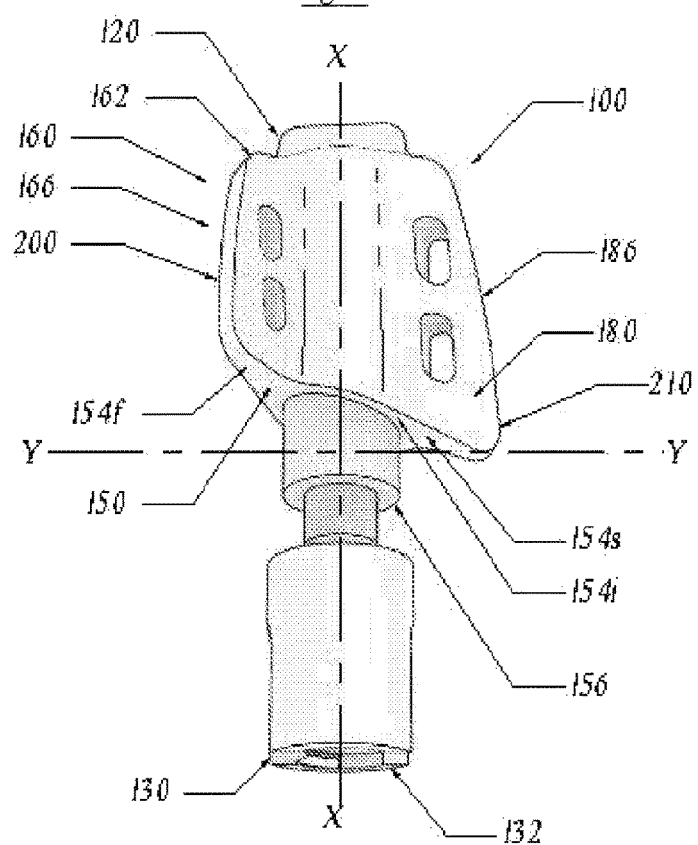
FIG. 8 is a perspective of the FIG. 7 preferred embodiment showing segments (154*i*, 154*f*, 154*s*) of surgeon facing end (154).

With a view toward FIGS. 5 and 6, surgical fastener (100) is provided with wedge-like tip (120) positioned at first end (152) of cutter (150). Wedge-like tip (120) is provided with frontal edge (122). Longitudinal axis (X-X) extends from the wedge-like tip (120) through the first end (152) and surgeon facing end (154) of cutter (150).

Cutter (150) includes first and second sections (160, 180) extending, in lateral planes, outwardly from the longitudinal axis (X-X). First and second sections (160, 180) can be distinct from wedge-like tip (120).

The first curvature (172) of the first section (160) extends the length of the cutter (150) from a first lengthwise end (162) proximate the first end (152) to a second lengthwise end (164) proximate the surgeon facing end (154). First curvature (172) has a first outermost point (200) distal from the longitudinal axis (X-X).

The second curvature (192) of the second section (180) extends the length of cutter (150) from a first lengthwise end (182) proximate the first end (152) to a second lengthwise end (184) proximate the surgeon facing end (154). Second curvature (182) includes a second outermost point (210) distal from the longitudinal axis (X-X).

In select preferred embodiments, the first outermost point (200) is at or near halfway of the first curvature (172) of the first section (160) and the second outermost point (210) is at or near halfway of the second curvature (192) of the second section (180), or the first outermost point (200) of the first curvature (172) of the first section (160) is proximate the surgeon facing end (154) and the second outermost point (210) of the second curvature (192) of the second section (180) is proximate the surgeon facing end (154) or the first outermost point (200) of the first curvature (172) is positioned between the first lengthwise end (162) and the second lengthwise end (164) of the first section (160) and the second outermost point (210) of the second curvature (192) is positioned between the first lengthwise end (182) and the second lengthwise end (184) of the second section (180) or any combination thereof.

First section (160) can include a first cutting edge (166) to cut a biological structure and a first noncutting edge (168) opposed from the first cutting edge (166) and a concave bend (170) relative to the opposed first noncutting edge (168). Second section (180) can include a second cutting edge (186) to cut the biological structure and a second noncutting edge (188) opposed from the second cutting edge (186) and a concave bend (190) relative to the opposed second noncutting edge (188).

In other preferred embodiments, surgeon facing end (154) is provided with an intermediate segment (154i) with the longitudinal axis (X-X) extending therethrough, a first segment (154f) connected with the intermediate segment (154i) and the second lengthwise end (164) of the first curvature (172) and a second segment (154s) connected with the intermediate segment (154i) and the second lengthwise end (184) of second curvature (192), wherein the intermediate segment (154i). In these preferred embodiments, intermediate, first and second segments (154i, 154f, 154s) create surgeon facing end (154).

Depending on engineering parameters, the first lateral planes associated with the first section (160) of cutter (150) can be oblique from the second lateral planes associated with the second section (180) cutter (150). In practice, first lateral planes can intersect second lateral planes at angles of from about 5 degrees to about 45 degree angles as measured from the first curvature (172) of first section (160) relative to the second lateral planes. Depending on medical parameters, the surgeon facing end (154) of cutter (150) can be sloped such that the first segment (154f is closer to the front end (152) of cutter (150) than the second segment (154s).

Select preferred embodiments of first section (160) of cutter (150) can be provided with one or more apertures (174f) Select preferred embodiments of second section (180) of cutter (150) can be provided with one or more apertures (174s).

After insertion of the surgical fastener (100) through a surgical incision (not shown), engagement of the surgically created cavity or the joint space (not shown) by the surgical fastener (100) and subsequent rotation of approximately 90 of degrees or more of cutter (150) relative to an engagement point of the surgically created cavity or joint space by wedge-like tip (120), surgical fastener (100) is positioned to resist pull out of surgical fastener (100) from the surgically created cavity or joint space.

Select preferred embodiments of the current invention have been disclosed and enabled as required by Title 35 of the United States Code and/or the Articles of the Patent Cooperation Treaty.

What is claimed is:

1. A surgical fastener (100) comprising:
   a) a wedge-like tip (120) positioned at a first end (152) of a cutter (150); the wedge-like tip (120) adapted to engage a joint space or a portion of a surgically created cavity or the joint space;
   b) a longitudinal axis (X-X) extending from the wedge-like tip (120) through the cutter (150) and a receiver (158) positioned in a surgeon facing end (154) of the cutter (150);
   the receiver (158) adapted to receive an apparatus distinct from the surgical fastener (100;
   c) the cutter (150) comprising a first section (160) and a second section (180) positioned on opposed sides of the longitudinal axis (X-X), wherein each section (160, 180) is distinct from the wedge-like tip (120) and extends the length of the cutter (150) from the first end (152) to the surgeon facing end (154) opposed from the first end (152) such that the first and second sections (160, 180) are adapted to cut radially relative to the longitudinal axis (X-X);
   d) the first section (160) further comprising a first cutting edge (166) to cut a biological structure and a first noncutting edge (168) opposed from the first cutting edge (166), wherein the first cutting edge (166) comprises a concave bend (170) relative to the opposed first noncutting edge (168) and a first curvature (172) extending between the first end (152) and the surgeon facing end (154) of the cutter (150), wherein, relative to the longitudinal axis (X-X), the first curvature (172) curves from a first point more proximate to the longitudinal axis (X-X) to a second point, proximate the surgeon facing end (154), more distant from the longitudinal axis (X-X) than the first point and the concave bend (170) runs from the first end (152) proximate the wedge-like tip (120) to the surgeon facing end (154); and
   e) the second section (180) further comprising a second cutting edge (186) to cut the biological structure and a second noncutting edge (188) opposed from the second cutting edge (186), wherein the second cutting edge (186) comprises a concave bend (190) relative to the opposed second noncutting edge (188) and a second curvature (192) extending between the first end (152) and the surgeon facing end (154) of the cutter (150), wherein, relative to the longitudinal axis (X), the second curvature (192) curves from a first point more proximate to the longitudinal axis (X) to a second point, proximate the surgeon facing end (154), more distant from the longitudinal axis (X-X) than the first point and the concave bend (190) runs from the first end (152) proximate the wedge-like tip (120) to the surgeon facing end (154), wherein rotation of the surgical implant (100) connects the surgical implant (100) to the joint space or a portion of the surgically created cavity and the joint space.

2. The surgical fastener (100) of claim 1, wherein:
   a) a frontal edge (122) of the wedge-like tip (120) can be either dull, sharp or a combination thereof; and/or
   b) length of the frontal edge (122) of the wedge-like tip (120) is less than length of the front end (152) of the cutter (150).

3. The surgical fastener (100) of claim 2, wherein the first and second sections (160, 180) comprise one or more apertures (174f, 174s).

4. The surgical fastener (100) of claim 3, wherein after insertion through a surgical incision, engagement of the surgically created cavity or the joint space by the surgical fastener (100) and subsequent rotation of approximately 90 of degrees of the cutter (150) relative to an engagement point of the wedge-like tip (120), the surgical fastener (100) is positioned to resist pull out of the surgical fastener (100) from the joint space or a portion of the surgically created cavity or the joint space.

5. A surgical fastener (100) comprising:
a) a wedge-like tip (120) positioned at a first end (152) of a cutter (150); the wedge-like tip (120) adapted to engage a joint space or a portion of a surgically created cavity or the joint space;
b) a longitudinal axis (X-X) extending from the wedge-like tip (120) through the cutter (150) and a head (130) connected with a surgeon facing end (154) of the cutter (150); the head (130) adapted to receive an apparatus distinct from the surgical fastener (100);
c) the cutter (150) comprising a first section (160) and a second section (180) positioned on opposed sides of the longitudinal axis (X-X), wherein each section (160, 180) is distinct from the wedge-like tip (120) and extends the length of the cutter (150) from the first end (152) to the surgeon facing end (154) opposed from the first end (152) such that the first and second sections (160, 180) are adapted to cut radially relative to the longitudinal axis (X-X);
d) the first section (160) further comprising a first cutting edge (166) to cut a biological structure and a first noncutting edge (168) opposed from the first cutting edge (166), wherein the first cutting edge (166) comprises a concave bend (170) relative to the opposed first noncutting edge (168) and a first curvature (172) extending between the first end (152) and the surgeon facing end (154) of the cutter (150), wherein, relative to the longitudinal axis (X-X), the first curvature (172) curves from a first point more proximate to the longitudinal axis (X-X) to a second point, proximate the surgeon facing end (154), more distant from the longitudinal axis (X-X) than the first point and the concave bend (170) runs from the first end (152) proximate the wedge-like tip (120) to the surgeon facing end (154); and
e) the second section (180) further comprising a second cutting edge (186) to cut the biological structure and a second noncutting edge (188) opposed from the second cutting edge (186), wherein the second cutting edge (186) comprises a concave bend (190) relative to the opposed second noncutting edge (188) and a second curvature (192) extending between the first end (152) and the surgeon facing end (154) of the cutter (150), wherein, relative to the longitudinal axis (X-X), the second curvature (192) curves from a first point more proximate to the longitudinal axis (X-X) to a second point, proximate the surgeon facing end (154), more distant from the longitudinal axis (X-X) than the first point and the concave bend (190) runs from the first end (152) proximate the wedge-like tip (120) to the surgeon facing end (154), wherein rotation of the surgical implant (100) connects the surgical implant (100) to the joint space or a portion of the surgically created cavity or the joint space.

6. The surgical fastener (100) of claim 5, wherein the first and second sections (160, 180) comprise one or more apertures (174*f*, 174*s*).

7. The surgical fastener (100) of claim 6, wherein the head (130) is a polyaxial head.

8. The surgical fastener (100) of claim 7 comprising an extender (156) extending from surgeon facing end (154) of cutter (150) and connected with the polyaxial head (130) for expanding the multiplanar range of motion of the polyaxial head (130).

9. The surgical fastener (100) of claim 5, wherein:
a) a frontal edge (122) of the wedge-like tip (120) can be either dull, sharp or a combination thereof; and/or b) length of the frontal edge (122) of the wedge-like tip (120) is less than length of the front end (152) of the cutter (150).

10. The surgical fastener (100) of claim 9, wherein after insertion through a surgical incision, engagement of the surgically created cavity or the joint space by the surgical fastener (100) and subsequent rotation of approximately 90 of degrees of the cutter (150) relative to an engagement point of the wedge-like tip (120), the surgical fastener (100) is positioned to resist pull out of the surgical fastener (100) from the joint space or a portion of the surgically created cavity or the joint space.

11. A surgical fastener (100) comprising:
a) a wedge-like tip (120) comprising a frontal edge (122); the wedge-like tip (120) positioned at a first end (152) of a cutter (150) and adapted to engage a joint space or a portion of a surgically created cavity or the joint space;
b) a longitudinal axis (X-X) extending from the wedge-like tip (120) through the first end (152) and a surgeon facing end (154) of the cutter (150);
c) the cutter (150) comprising:
 i) a first section (160) distinct from the wedge-like tip (120) and a second section (180) distinct from the wedge-like tip (120); the first and second sections (160, 180) extending outward in lateral planes from the longitudinal axis (X-X);
 ii) a first curvature (172) of the first section (160) extending the length of the cutter (150) from a first lengthwise end (162) proximate the first end (152) to a second lengthwise end (164) proximate the surgeon facing end (154); the first curvature (172) including a first outermost point (200) distal from the longitudinal axis (X-X); and
 iii) a second curvature (192) of the second section extending the length of the cutter (150) from a first lengthwise end (182) proximate the first end (152) to a second lengthwise end (184) proximate the surgeon facing end (154); the second curvature (182) including a second outermost point (210) distal from the longitudinal axis (X-X);
d) the first section (160) further comprising a first cutting edge (166) to cut a biological structure and a first noncutting edge (168) opposed from the first cutting edge (166), wherein the first cutting edge (166) comprises a concave bend (170) relative to the opposed first noncutting edge (168);
e) the second section (180) further comprising a second cutting edge (186) to cut the biological structure and a second noncutting edge (188) opposed from the second cutting edge (186), wherein the second cutting edge (186) comprises a concave bend (190) relative to the opposed second noncutting edge (188); and
f) the surgeon facing end (154) further comprising:
 i) an intermediate segment (154*i*) with the longitudinal axis (X-X) extending therethrough;
 ii) a first segment (154*f*) connected with the intermediate segment (154*i*) and the second lengthwise end (164) of the first curvature (172); and
 iii) a second segment (154*s*) connected with the intermediate segment (154*i*) and the second lengthwise end (184) of second curvature (192), wherein the intermediate segment (154*i*), the first segment (154*f*) and the second segment (154*s*) create the surgeon facing end (154) consisting of the intermediate, first and second segments (154*i*, 154*f*, 154*s*).

12. The surgical fastener (100) of claim 11, wherein after insertion through a surgical incision, engagement of the surgically created cavity or the joint space by the surgical fastener (100) and subsequent rotation of approximately 90 of degrees of the cutter (150) relative to an engagement point of the wedge-like tip (120), the surgical fastener (100) is positioned to resist pull out of the surgical fastener (100) from the joint space or a portion of the surgically created cavity or the joint space.

13. The surgical fastener (100) of claim 12, wherein the first and second sections (160, 180) comprise one or more apertures (174f, 174s).

14. The surgical fastener (100) of claim 13, wherein:
a) a frontal edge (122) of the wedge-like tip (120) can be either dull, sharp or a combination thereof; and/or
b) length of the frontal edge (122) of the wedge-like tip (120) is less than length of the front end (152) of the cutter (150).

15. The surgical fastener (100) of claim 14, wherein:
a) the first outermost point (200) is at or near halfway of the first curvature (172) of the first section (160) and the second outermost point (210) is at or near halfway of the second curvature (192) of the second section (180); or
b) the first outermost point (200) of the first curvature (172) of the first section (160) is proximate the surgeon facing end (154) and the second outermost point (210) of the second curvature (192) of the second section (180) is proximate the surgeon facing end (154); or
c) the first outermost point (200) of the first curvature (172) is positioned between the first lengthwise end (162) and the second lengthwise end (164) of the first section (160) and the second outermost point (210) of the second curvature (192) is positioned between the first lengthwise end (182) and the second lengthwise end (184) of the second section (180).

16. The surgical fastener (100) of claim 15 comprising a receiver (158) extending inward from the intermediate segment (154i) of surgeon facing end (154) of the cutter (150), wherein the receiver (158) is adapted to receive an apparatus distinct from the surgical fastener (100).

17. The surgical fastener (100) of claim 16, wherein the surgeon facing end (154) is sloped such that the first segment (154f) is closer to the front end (152) of cutter (150) than the second segment (154s).

18. The surgical fastener (100) of claim 15 comprising a head (130) connected with the intermediate segment (154i) of surgeon facing end (154) of the cutter (150), wherein the head (130) is adapted to receive an apparatus distinct from the surgical fastener (100).

19. The surgical fastener (100) of claim 18, wherein the head (130) is a polyaxial head and the surgical fastener (100) further comprises an extender (156) extending from the intermediate segment (154i) of surgeon facing end (154) of the cutter (150) and connected with the polyaxial head (130) for expanding the multiplanar range of motion of polyaxial head (130).

20. The surgical fastener (100) of claim 19, wherein the surgeon facing end (154) is sloped such that the first segment (154f) is closer to the front end (152) of cutter (150) than the second segment (154s).

* * * * *